United States Patent
Sheffer et al.

(10) Patent No.: US 9,283,344 B2
(45) Date of Patent: Mar. 15, 2016

(54) APPARATUS, SYSTEM, AND METHOD OF FLUID DELIVERY CONNECTION

(75) Inventors: Garrett Austin Sheffer, Hoboken, NJ (US); Paul A. Kendrick, Morristown, NJ (US)

(73) Assignee: CAREFUSION CORPORATION, San Diego, CA (US)

( * ) Notice: Subject to any disclaimer, the term of this patent is extended or adjusted under 35 U.S.C. 154(b) by 638 days.

(21) Appl. No.: 13/342,558

(22) Filed: Jan. 3, 2012

(65) Prior Publication Data
US 2013/0167841 A1      Jul. 4, 2013

(51) Int. Cl.
| | |
|---|---|
| *A61M 16/00* | (2006.01) |
| *A61M 16/08* | (2006.01) |
| *A61M 39/10* | (2006.01) |
| *F16L 37/098* | (2006.01) |

(52) U.S. Cl.
CPC ....... *A61M 16/0816* (2013.01); *A61M 39/1011* (2013.01); *F16L 37/0982* (2013.01); *A61M 2039/1027* (2013.01); *A61M 2039/1033* (2013.01)

(58) Field of Classification Search
CPC . A61M 16/08; A61M 16/0463; A61M 16/06; A61M 16/0683; A62B 9/04
USPC ............. 604/533, 534, 535, 284; 128/200.24, 128/202.27, 204.18, 204.25, 207.14, 128/207.15, 207.16, 207.17, 911, 912; 403/348, 349; 285/242, 314, 34, 322, 285/243, 255, 257, 3
See application file for complete search history.

(56) References Cited

U.S. PATENT DOCUMENTS

| | | | |
|---|---|---|---|
| 1,006,190 A | 10/1911 | Estell et al. | |
| 4,846,167 A | 7/1989 | Tibbals | |
| 4,895,570 A * | 1/1990 | Larkin | 604/411 |
| 5,276,280 A * | 1/1994 | Ball | 174/652 |
| 5,282,463 A | 2/1994 | Hammersley | |
| 5,509,911 A | 4/1996 | Cottone et al. | |
| 6,257,278 B1 | 7/2001 | Danielson et al. | |
| 6,585,016 B1 | 7/2003 | ***Falligant et al. | |

(Continued)

FOREIGN PATENT DOCUMENTS

| | | |
|---|---|---|
| CN | 1118853 A | 3/1996 |
| CN | 1940372 A | 4/2007 |

(Continued)

OTHER PUBLICATIONS

Search and Written Opinion from EP Application No. 12198150.0 dated May 2, 2013.

(Continued)

*Primary Examiner* — Jason Flick
*Assistant Examiner* — Elliot S Ruddie
(74) *Attorney, Agent, or Firm* — McDermott Will & Emery LLP

(57) ABSTRACT

A fluid delivery connection includes a cuff to engage a port. A finger extends away from the cuff, and the finger is configured to interact with the port. A locking sleeve is movably disposed at least partially about the cuff and the finger. The locking sleeve is selectively movable between an unlocked configuration wherein the finger is movable and a locked configuration wherein the finger is secured to the port. A method of connection to a gas port includes moving a locking sleeve of a connector into an unlocked configuration. A finger of the connector is translated along the gas port and the locking sleeve is moved into a locked configuration.

10 Claims, 7 Drawing Sheets

(56) References Cited

U.S. PATENT DOCUMENTS

| | | |
|---|---|---|
| 6,929,041 B2 | 8/2005 | Falligant et al. |
| 7,168,467 B2 | 1/2007 | Turker et al. |
| 7,241,974 B2 | 7/2007 | Reusche et al. |
| 7,287,561 B2 | 10/2007 | Turker et al. |
| 7,389,801 B2 | 6/2008 | Turker et al. |
| 7,490,607 B2 | 2/2009 | Bottom et al. |
| 7,543,858 B1 * | 6/2009 | Wang .......................... 285/314 |
| 2004/0000788 A1 | 1/2004 | Cronley |
| 2004/0150223 A1 * | 8/2004 | Campau ........................ 285/308 |
| 2008/0012314 A1 | 1/2008 | Harger et al. |
| 2010/0090150 A1 | 4/2010 | Readman |

FOREIGN PATENT DOCUMENTS

| | | |
|---|---|---|
| CN | 101048613 A | 10/2007 |
| DE | 102007020556 B3 | 6/2006 |
| EP | 0340194 A1 | 11/1989 |
| GB | 2186652 A | 8/1987 |

OTHER PUBLICATIONS

Chinese First Office Action for Application No. 201310001190.4, dated Dec. 2, 2015, 21 pages.

* cited by examiner

US 9,283,344 B2

APPARATUS, SYSTEM, AND METHOD OF FLUID DELIVERY CONNECTION

BACKGROUND

The present disclosure is related to the field of mechanical ventilation. More specifically, the present disclosure is related to connectors for use in mechanical ventilation.

Mechanical ventilation is a therapeutic technique commonly used in critical care medical settings whereby the physical acts of inspiration and expiration by a patient are performed or assisted by a mechanical device, namely, a ventilator.

The ventilator delivers medical gas to the patient through a breathing circuit. The medical gas delivered to the patient may include, but is not limited to, air. Additionally, the medical gas may be enriched with oxygen or other gases in order to meet specific therapeutic requirements of the patient.

In some settings, an anesthesia delivery device may be used in parallel with, connected to, or integrated with the ventilator such as to deliver vaporized anesthetic agents to the patient to provide anesthesia therapy.

SUMMARY OF THE INVENTION

In accordance with an embodiment of a fluid delivery connection disclosed herein, the embodiment of the fluid delivery connection includes a cuff that is configured to engage a fluid port and connect to a fluid delivery circuit. A finger extends away from the cuff and is configured to interact with the fluid port. In accordance with the embodiment, a locking sleeve is movably disposed at least partially about the cuff and the finger and the locking sleeve is selectively movable between an unlocked configuration wherein the finger is movable and a locked configuration wherein the figure is secured to the fluid port.

In an embodiment of gas delivery system as disclosed herein, a breathing circuit is configured to be connected to a patient to deliver medical gas to the patient. In accordance with the embodiment, a cuff with a first end removably engages the breathing circuit and a second end removably engages a cylindrical gas port and the cuff creates a fluid connection between the cylindrical gas port and the breathing circuit. In further accordance with the embodiment, a finger includes a tab that selectively engages the annular cutout of the cylindrical gas port and a locking sleeve is disposed about at least a portion of the cuff and is selectively movable between an unlocked configuration wherein the finger is movable and the lock configuration when the finger is secured to the cylindrical gas port and the tab is secured to the annular cutout of the cylindrical gas port.

In an embodiment of a method of universal connections to a fluid port, a locking sleeve of a connector is moved into an unlocked configuration and the finger is deflected radially outwards from the exterior of the fluid port and translated coaxially along the exterior of the fluid port. A fluid connection is established between the gas port and a cuff of the connector. In accordance with an embodiment disclosed herein, the locking sleeve is moved into a locked configuration, the finger engages the locking sleeve of the connector, and radial outward deflection of the finger away from the fluid port is prevented.

BRIEF DESCRIPTION OF THE DRAWINGS

The drawings illustrate the best mode presently contemplated of carrying out the disclosure. In the drawings.

DETAILED DESCRIPTION

Figure 1:
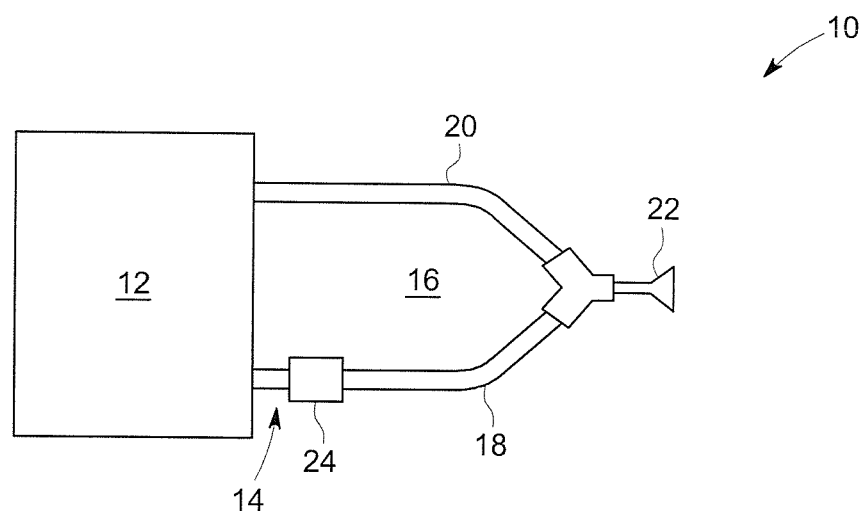
FIG. 1 is a system diagram of an embodiment of a gas delivery system.

FIG. 1 depicts a fluid delivery system 10. The fluid delivery system 10 includes a mechanical ventilator 12. The fluid delivery system 10 is exemplarily depicted herein as a medical gas delivery system with the fluid being one or more medical gases. However, this is not intended to be limiting on the scope of the system within which the connector disclosed herein may be used. The mechanical ventilator 12 may be any of a variety known to one of ordinary skill in the art. In some embodiments of the mechanical ventilator 12, an internal manifold (not depicted) receives one or more constituent medical gases, including, but not limited to, air, oxygen, nitrogen, carbon dioxide, nitric oxide, or helium. The mechanical ventilator mixes these gases into a combination medical gas that is delivered to the patient. In still further embodiments of the mechanical ventilator 12, an anesthesia delivery system is incorporated with the mechanical ventilator such that gaseous anesthetic agents can also be combined in the medical gas delivered to the patient. In alternative embodiments, an anesthesia system may be used independently instead of the medical ventilator.

The mechanical ventilator 12 includes a fluid port 14. It has been observed by the applicant that mechanical ventilator products from different manufacturers or different models from the manufacturer may use gas ports of varying dimensions, shapes, or sizes. This can lead to incompatibility between various connections or conduits to be connected to the mechanical ventilator which creates waste and redundancy, particularly in clinical settings that use devices with different gas ports. The International Organization for Standardization (ISO) has defined that independent from other dimensional characteristics of gas ports, each gas port must have an undercut on the gas port.

The fluid delivery system 10 of FIG. 1 further depicts a fluid delivery circuit 16, which in the exemplary embodiment is a breathing circuit 16 that includes an inspiratory limb 18, an expiratory limb 20, and a patient connection 22. The inspiratory limb 18 is fluidly connected to the gas port 14 by a connector 24, which will be described in further detail herein.

While FIG. 1 depicts one embodiment of a breathing circuit 16, wherein the expiratory limb 20 connects back to the mechanical ventilator 12 by a separate conduit, it is to be recognized that various alternative embodiments of breathing circuits 16, as known to those of skill in art, are contemplated within the scope of the present disclosure. In one non-limiting example, other components (e.g. filters or humidifiers) can be incorporated with the breathing circuit between the mechanical ventilator 12 and the patient connection 22. In a further non-limiting example of such an alternative breathing circuit, the inspiratory limb and the expiratory limb are integrally formed in a dual lumen conduit. In such a dual lumen conduit embodiment, an external manifold (not depicted) connects the combined inspiratory limb and expiratory limb to separate connections to the mechanical ventilator 12. In a still further embodiment of the breathing circuit 16, the expiratory limb, rather than returning to the mechanical ventilator 12, may directly vent to the ambient air.

While not depicted in FIG. 1, it is to be understood that in alternative embodiments of the mechanical ventilator 12, an expiratory gas port (not depicted) similar in construction to that of the gas port 14 form the connection of the expiratory limb 20 to the mechanical ventilator 12. In such an embodiment, a second connector (similar to connector 24) and as disclosed herein could be used to connect the expiratory limb 20 to the mechanical ventilator 12. It is further to be understood that embodiments are not limited to the connection between the breathing circuit and the mechanical ventilator. In other embodiments, other components can be connected using the connection as disclosed herein. In one exemplary embodiment, a filter is disposed between the breathing circuit and the mechanical ventilator and includes an embodiment of the connector disclosed herein to connect to the mechanical ventilator. In another exemplary embodiment, a patient connection 22 includes an embodiment of the connector as disclosed herein to connect to the breathing circuit. In a still further non-limiting embodiment, the mechanical ventilator 12 includes an embodiment of the connector, such that the mechanical ventilator 12 can universally accept a wide range of ports on components such as filters or breathing circuits.

Figure 2:
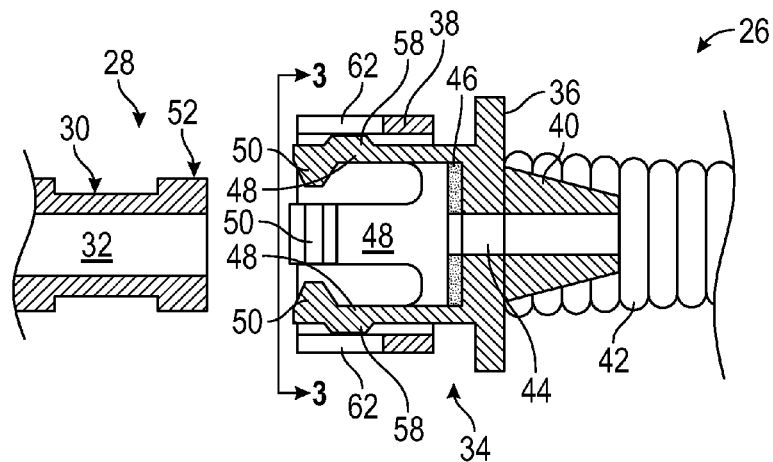
FIG. 2 is a cut away view of a gas port and a connector in accordance with an embodiment of the gas delivery system.

FIG. 2 depicts a more detailed embodiment of a fluid delivery system 26. The fluid delivery system 26 includes a fluid or gas port 28, which is exemplarily a gas port of a mechanical ventilator 12, but would be recognized by one of ordinary skill in the art to be a fluid port of any of a variety of fluid sources, and not specifically limited to those of medical gases such as with mechanical ventilators or anesthesia delivery systems. Exemplarily, the gas port 28 may be 22 millimeters in diameter and include an annular cutout 30; however, it will be recognized that these are non-limiting on the scope of gas ports 28 within the present disclosure. The gas port 28 further includes a bore 32 that is disposed for gas to travel therethrough.

The fluid delivery system 26 further includes a connector 34. The connector 34 includes two portions, a cuff 36 and a locking sleeve 38.

The cuff 36 includes a conduit connection 40 at one end that is disposed for connection to a conduit 42, exemplarily that of a breathing circuit. The conduit connection 40 includes a bore 44 therethrough that is configured to align with the bore 32 of the gas port 28 such as to form a fluid connection between the gas port 28 and the conduit 42. Embodiments of the connector 34 further include a seal 46 which is exemplarily a gasket or O-ring, exemplarily constructed of an elastomeric material that facilitates a fluid seal between the gas port 28 and the cuff 36. In alternative embodiments, the cuff 36 is constructed in a shape or of a material to at least partially deform to create a fluid seal about the gas port 28.

The cuff 36 further includes at least one finger 48 that extends away from the cuff 36 in the direction of the gas port 28. In the embodiment of the connector 34 depicted in FIG. 2, four fingers 48 are used; however, this is merely exemplary and alternative embodiments may use any number of fingers, including embodiments with one finger, two fingers, three fingers, or more than four fingers.

The finger 48 includes a tab 50 that extends radially inward from the finger 48. The tab 50 is constructed such as to engage the annular cutout 30 of the gas port 28. The finger 48 is resiliently constructed such that the finger 48 can deform radially outward such that when the connector 34 is moved in the direction of the gas port 28, the finger 48 can deflect radially outward such that at least a portion of the finger 48 and the tab 50 can move past the front end 52 of the gas port 28, before returning radially inward once the tab 50 is aligned with the annular cutout 30.

Figure 3:
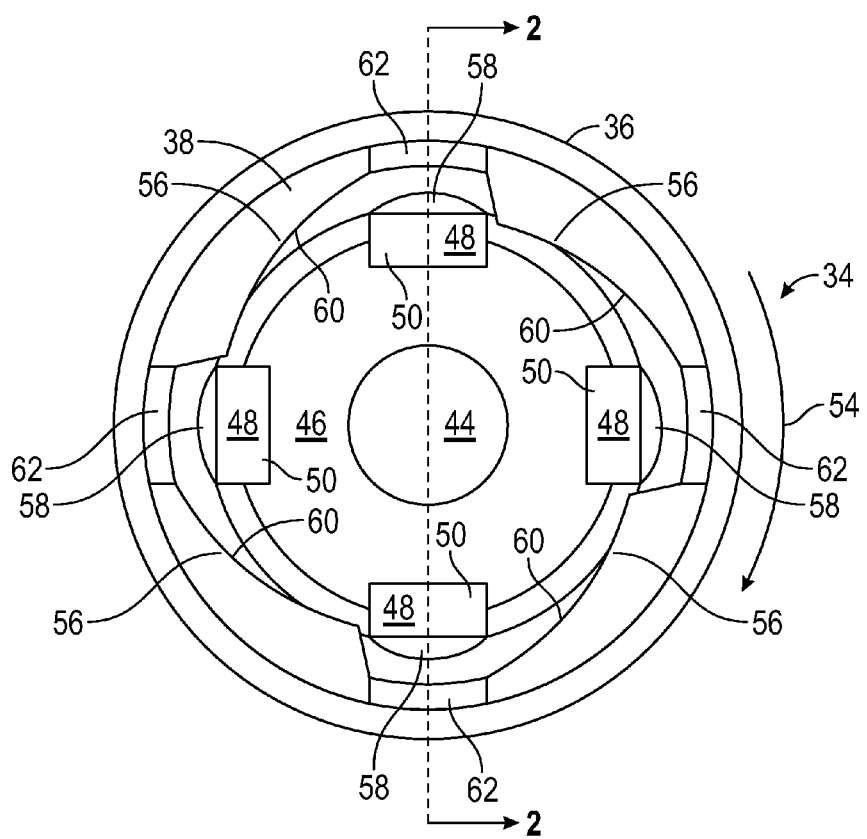
FIG. 3 is a cut away view of the embodiment of the connector of FIG. 2 taken along the line 3-3.

The locking sleeve 38 is circumferentially disposed about at least a portion of the connector 34, and at least a portion of the finger 48. The locking sleeve 38 performs the function of preventing the outward deflection of the finger 48 and tab 50, thereby securing the connector 34 to the gas port 28. In the embodiment of the locking sleeve 38 depicted in FIGS. 2 and 3, the locking sleeve 38 is configured to be rotated in the direction of arrow 54 to prevent the linger 48 and tab 50 from deflecting radially outward, and in some embodiments, deflect the finger 48 and tab 50 slightly radially inward to further secure the connector 34 to the gas port 28.

The locking sleeve 38 includes a ramp 56 that progressively engages a ridge 58 of the finger 48. It is to be understood that in alternative embodiments, the locking sleeve 38 includes more than one ramp 56. As depicted in the embodiment of the connector 34 of FIG. 3, the locking sleeve 38 includes four ramps 56, one ramp 56 that is associated with each of the four fingers 48 that respectively each include a ridge 58. As the locking sleeve 38 is rotated about the cuff 36 in the direction of arrow 54, the ramp 56 progressively engages the ridge 58, thereby applying a force radially inward on the ridge 58 and associated finger 48. The locking sleeve 38 is therefore rotatably movable between a locked configuration wherein the interior surface 60 of the locking sleeve 38 engages the finger 48 to retain the finger 48 from movement radially outward and an unlocked configuration wherein the finger 48 is permitted to move radially outward. In the embodiment of the locking sleeve 38 depicted in FIGS. 2 and 3, the locking sleeve 38 further includes cutout 62 that aligns with the finger 48 when the locking sleeve 38 is in the unlocked configuration. The cutout 62 further permits the finger 48 to deflect radially outward beyond the circumference defined by the interior surface 60 of the locking sleeve 38.

While the locking sleeve 38 has been disclosed herein as including one or more ramps 56 that modify the location of the interior surface 60 of the locking sleeve 38, it is to be noted that the effect of the one or more ramps 56 is to create an interior surface 60 of the locking sleeve 38 with a varying inside diameter. In alternative embodiments of the locking sleeve, the interior diameter of the locking sleeve may be any of a variety of shapes or constructions such as to have a varying interior diameter that will effectively define a locked configuration wherein alignment of the narrow interior diameter with one or more finger will cause the interior surface 60 to restrain the one or more finger 48 from radially outward movement, while alignment of a generally elongated interior diameter removes the interior surface from engagement with the one or more finger 48 in the unlocked configuration that permits movement of the one or more finger 48 in a radially outward direction.

In one embodiment, the interior surface 60 of the locking sleeve 38 is an ellipse. In such embodiments, the entire locking sleeve 38 itself can be in the shape an ellipse or the locking sleeve 38 can maintain an alternative shape defined by an exterior surface while an elliptical shape is defined by the interior surface. It will be recognized that the above description of an elliptical interior surface is not intended to be limiting on the scope of the locking sleeve construction, and other geometric shapes with varying cross sectional diameters may be used within the scope of the present disclosure.

Figure 4:
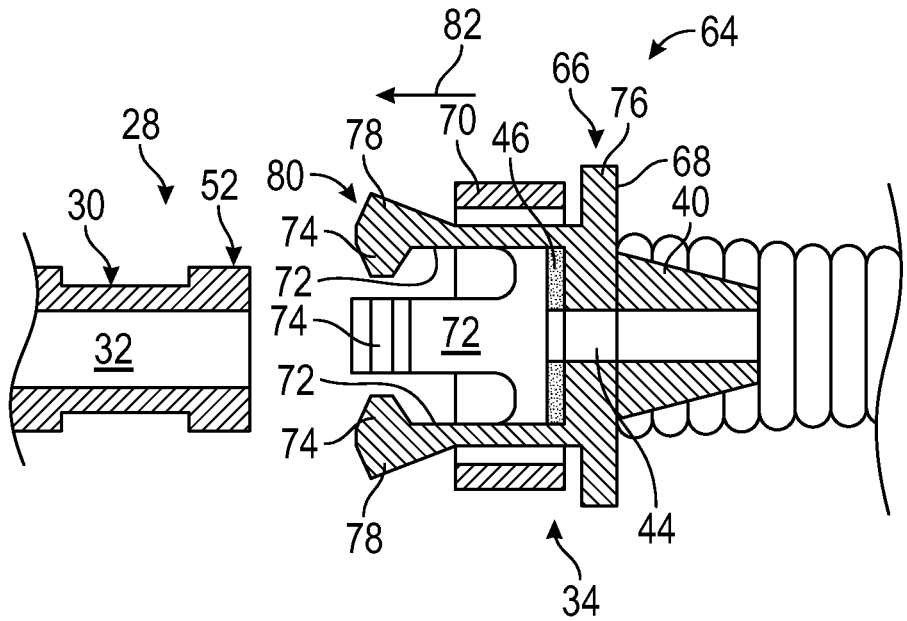
FIG. 4 depicts a gas port and a connector in accordance with an alternative embodiment of the gas delivery system in a locked configuration.
Figure 5:
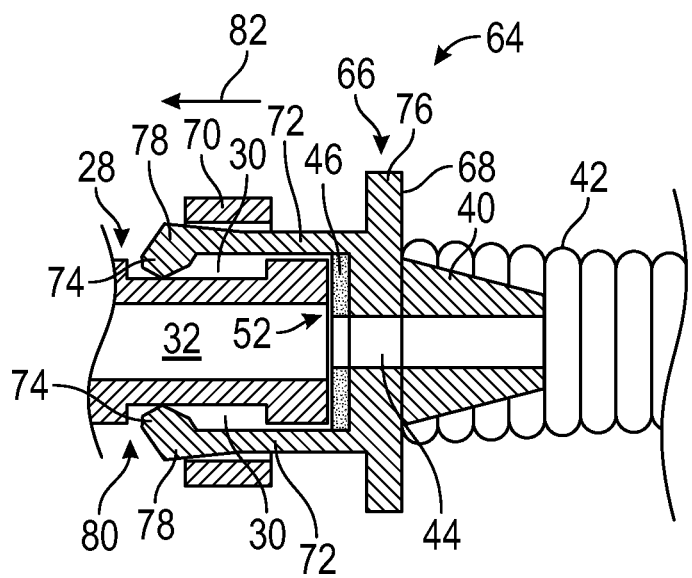
FIG. 5 depicts a gas port and connector of the embodiment of FIG. 4 in a locked configuration.

FIGS. 4 and 5 depict an alternative embodiment of a gas delivery system 64. It is to be noted that in the present disclosure, like reference numerals have been used between figures in order to identify like structures and features such as to reduce redundancy within the present disclosure. FIGS. 4 and 5 depict an alternative embodiment of a connector 66. The alternative embodiment of the connector 66 includes alternative constructions of the cuff 68 and the locking sleeve 70 as opposed to those as found in the connector 34 depicted in FIGS. 2 and 3. FIG. 4 depicts the connector 66 in an unlocked configuration, while FIG. 5 depicts the connector 66 in a locked configuration in engagement with the gas port 28.

The connector 66 includes a finger 72 that extends away from the conduit connection 40, in the direction of the gas port 28. Similar to the fingers of FIGS. 2 and 3, the finger 72 terminates in a tab 74 that projects radially inward from the finger 72. The finger 72 is flexible or deformable such as to deflect radially outward such as to move the tab 74 past the front end 52 of the gas port 28 and into the annular cutout 30 of the gas port 28. In the unlocked configuration, the locking sleeve 70 is in a position radially exterior of the finger 72 and in a position along the finger 72 proximal the conduit connection 40. In the embodiment of the connector 66, when the locking sleeve 70 is in the unlocked configuration, the locking sleeve 70 is adjacent a collar 76 of the cuff 68. This permits the finger 72 to deform radially outward. Although not depicted in the embodiment shown in FIGS. 4 and 5, the locking sleeve 70 may further include cutouts such that when the locking sleeve 70 is in the unlocked configuration, outward deflection of the finger 72 is further uninhibited by the locking sleeve 70.

In the embodiment of the cuff 68 depicted in FIGS. 4 and 5, the finger 72 further includes a ramp 78 that extends radially away from the finger 72 as the ramp 78 approaches the gas port end 80 of the connector 66. When the locking sleeve 70 is moved in the direction of arrow 82 from the unlocked configuration shown in FIG. 4 to the locked configuration shown in FIG. 5, the locking sleeve 70 engages the ramp 78. The engagement of the ramp 78 by the locking sleeve 70 in some embodiments restrains the finger 72 from radially outward deflection, while in alternative embodiments, the engagement of the ramp 78 by the locking sleeve 70 causes a radially inwardly deflection of the finger 72 and tab 74. Thus, when the locking sleeve 70 is in the locked configuration, the connector 66 is restrained, as depicted in FIG. 5, from releasing engagement with the gas port 28. Alternatively the ramp 78 could be aligned axially about the outside circumference of the finger in an embodiment wherein the locking sleeve 70 rotates.

It is to be understood that alternative embodiments or variations of the connector 66 as depicted in FIGS. 4 and 5 are considered to be within the scope of the present disclosure. In some such embodiments, the locking sleeve 70 moves generally in the direction of arrow 82 with a rotational component rather than a purely translational motion. Such a rotational component to the movement of the locking sleeve 70, may include the engagement of cooperative threads (not depicted) found on the ramp 78 and the locking sleeve 70. This can create a mechanical advantage as the rotating screw fit between the locking sleeve 70 and the ramp 78 of the finger 72 and facilitate a greater tightening of the locking sleeve. In an alternative embodiment wherein the motion of the locking sleeve 70 includes a rotational component, the locking sleeve 70 may include a cutout or slot, exemplarily as depicted in the locking sleeve of FIGS. 2 and 3, wherein the cutout is aligned with the finger 72 when in the unlocked configuration and the cutout is out of alignment with the finger 72 in the locked configuration. In one such embodiment, the rotation of the locking sleeve 70 may sequentially cover up or expose visual indications on the finger 72 that indicate a current configuration of the locking sleeve 70 (e.g. locked or unlocked). A visual indication of an unlocked configuration is shown when the locking sleeve is in an unlocked configuration and a visual indication of a locked configuration is shown when the locking sleeve is in a locked configuration. In alternative embodiments, the visual indications may be located on other components such as, but not limited to, on the locking sleeve 70, cuff 68, or collar 76.

In other embodiments, the ramp 78 may include alternative configurations, exemplarily, but not limited to, the ramp may be located on the locking sleeve 70 adjacent the finger 72. As the locking sleeve 70 is moved in the direction of arrow 82, the ramp on the locking sleeve (not depicted) may engage a ridge or other structure (not depicted) extending radially outwards from the finger 72 in order to achieve the same effect as described above. In a still further embodiment, the finger 72 does not include a ramp 78 and rather the locking sleeve 70 moves along the finger 72 in the direction of arrow 82, and the circumference defined by an interior surface of the locking sleeve 70 restricts any radially outward movement of the finger to that defined by the locking sleeve.

In a still further embodiment, a biasing element (not depicted), exemplarily a spring may be disposed between the collar 76 and the locking sleeve 70, such as to bias the locking sleeve 70 in the locked configuration by being pushed away from the collar 76 in the direction of arrow 82. Therefore, if a clinician or technician seeks to use the connector 66, the clinician or technician must first overcome the bias created by the spring to move the locking sleeve into the unlocked configuration before engaging the gas port 28 with the connector 66 and releasing the locking sleeve 70 to return in the direction of arrow 82 to the biased position. In an alternative embodiment, the biasing element holds the locking sleeve in a normally unlocked configuration, requiring a clinician to overcome the bias to lock the connector.

While not depicted in FIGS. 4 and 5, still further embodiments of the ramp 78 and the locking sleeve 70 may include matingly disposed teeth or steps such as to create a ratchet or locking action as the locking sleeve 70 is moved in the direction of arrow 82. Such an embodiment would progressively tighten the locking sleeve 70 about the finger 72 and also to retain the locking sleeve 70 in a locked configuration about the finger 72. The locking sleeve can be released from such engagement with the finger 72 in a variety of ways, one non-limiting example thereof being rotating the locking sleeve 70 to move the mating teeth or steps (not depicted) out of alignment with the ramp 78, thereby permitting the return of the locking sleeve 70 to the unlocked configuration.

In an alternative embodiment, the locking sleeve 70 may be configured with cutout (exemplarily depicted at 62 of FIGS. 2 and 3) that permit at least a portion of the ramp 78 to be coplanar with the locking sleeve 70. A mating relationship between the coplanar portions of the locking sleeve 70 and the ramp 78, exemplarily a tab that extends from the locking sleeve 70 into a mating groove (not depicted) along the coplanar side of the ramp 78, applies the mechanical force radially inward on the finger 72 as the locking sleeve 70 is translated in the direction of arrow 82.

Figure 6:
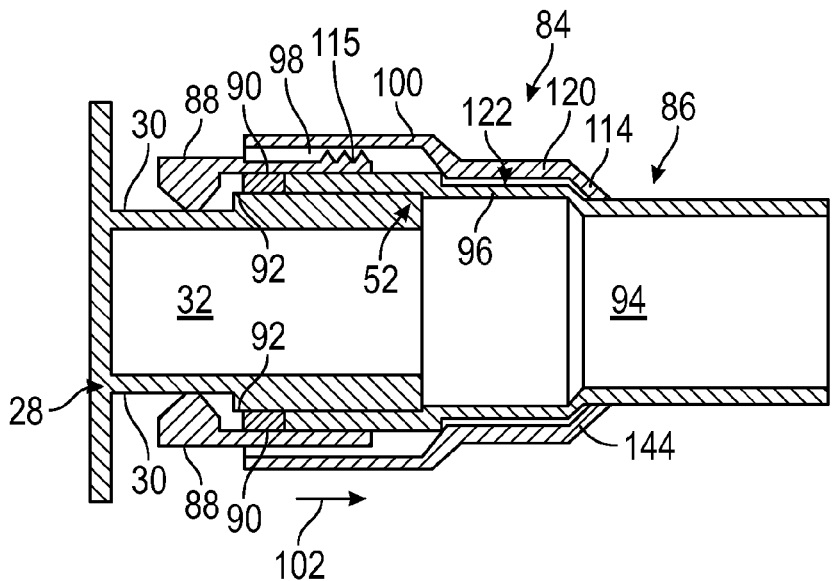
FIG. 6 is a cut away view of a gas port and connector in accordance with an alternative embodiment of the gas delivery system.

FIG. 6 depicts an alternative embodiment of a gas delivery system 84. The gas delivery system 84 includes a connector 86 of an alternative construction in a manner as to perform an additional function from those connectors described above. Namely, the connector 86 is configured such as to connect to the gas port 28, but then is additionally operable to remove any slack that exists between the tab 88 of the finger 90 of the connector 86 and a toe 92 of the front end 52 of the gas port 28. By removing the slack in the annular cutout 30 between the tab 88 of the finger 90 and the toe 92 of the gas port 28, the connector 86 further ensures that beyond preventing disconnection of the connector 86 from the gas port 28, the connector 86 maintains a fluid seal between the bore 32 of the gas port 28 and the bore 94 of the connector 86.

The connector 86 differs from previously disclosed connectors in that the connector 86 is constructed of three components, a cuff 96, a latch 98, and a locking sleeve 100. As can be seen from the cross sectional view depicted in FIG. 6, the cuff 96 engages the gas port 28 to align and fluidly seal the bore 94 of the connector 86 with the bore 32 of the gas port 28. The latch 98 is disposed radially outward from the cuff 96. A finger 90 of the latch 98 extends away from the cuff 96 in the direction of the gas port 28. While FIG. 6 depicts two fingers 90, it is understood that any number of fingers may be used in embodiments within the scope of the present disclosure. The tab 88 on the finger 90 engages the annular cutout 30 of the gas port 28. In an embodiment, the finger 90 is constructed to be radially deformable such that the finger 90 and tab 88 can deflect radially outward to move about the toe 92 of the front end 52 of the gas port 28 and into engagement with the annular cutout 30.

The locking sleeve 100 is circumferentially disposed about at least a portion of the cuff 96 and at least a portion of the latch 98. The locking sleeve 100 retains both the cuff 96 and the latch 98 such as to hold the connector 86 together. As will be described in further detail herein with respect to FIGS. 7 and 8, the locking sleeve 100 is operable in an unlocked configuration wherein the latch 98 is held between the cuff 96 and the locking sleeve 100 in a movable manner. The locking sleeve 100 is further operable in a locked configuration wherein the latch 98 is drawn towards the cuff 96 in the direction of arrow 102 in order to remove any slack in the engagement between the connector 86 and the gas port 28, particularly in order to place the tab 88 in engagement with both the annular cutout 30 and the toe 92 of the gas port 28.

Figure 7:
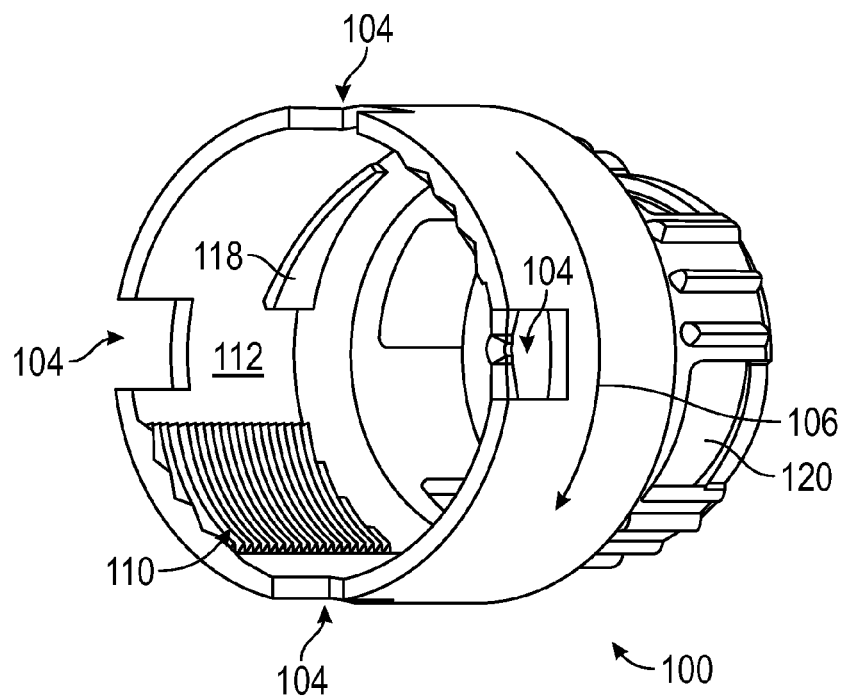
FIG. 7 is a perspective view of a locking sleeve in accordance with an embodiment of the embodiment of FIG. 6.
Figure 8:
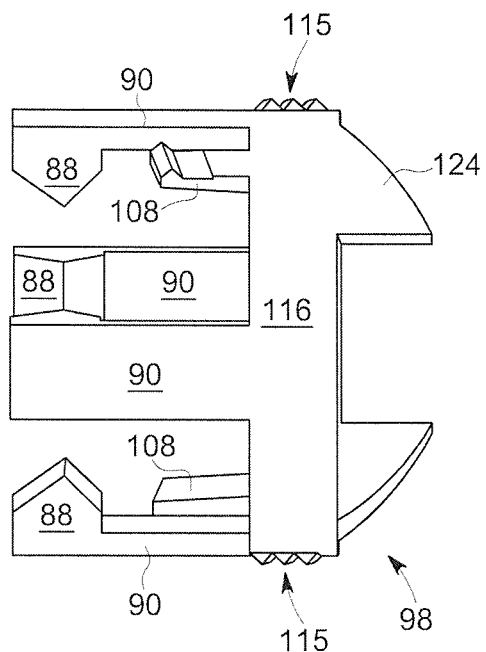
FIG. 8 depicts a latch in accordance with an embodiment of the alternative embodiment depicted in FIG. 6.

FIG. 7 depicts a more detailed embodiment of a locking sleeve 100. FIG. 8 depicts a more detailed embodiment of a latch 98. The following description will refer to FIGS. 6-8 in order to describe these embodiments, and the operation thereof. It is to be recognized that this is a merely exemplary embodiment and alternative embodiments use only some of the features of these embodiments as described herein and still remain within the scope of the present disclosure.

After the connector 86 engages the gas port 28, the locking sleeve 100 is still in the unlocked configuration and slack remains between the tab 88 and the toe 92. In such an unlocked configuration, cutout 104 in the locking sleeve 100 is in alignment with the finger 90 of the latch 98. Similar to embodiments as described above, the alignment of the cutout 104 with the finger 90 permits radially outward deflection such that the tab 88 can move past the toe 92 and into the annular cutout 30 of the gas port 28.

In order to move the locking sleeve 100 from the unlocked configuration to the locked configuration, the locking sleeve is rotated, exemplarily in the direction of arrow 106. First, the rotation of the locking sleeve 100 in the direction of arrow 106 places the cutout 104 out of alignment with the finger 90, which therefore inhibits any further radially outward deflection by the finger 90, and holds the finger 90 and tab 88 in contact with the annular cutout 30.

As shown in FIG. 8, the latch 98 includes a pawl 108. In an embodiment, the latch 98 includes more than one pawl 108. As a non-limiting example, the latch 98 depicted in FIG. 8 includes two pawls 108. As the locking sleeve 100 is rotated in the direction of arrow 106, the pawl 108 rides threads 110 located on an interior surface 112 of the locking sleeve 100. Therefore, the rotating engagement of the pawl 108 with the threads 110 draw the latch 98, including the finger 90 and tab 88 towards the cuff 96. The locking sleeve 100 includes a fitting 114 (FIG. 6) that engages the cuff 96 such as to restrict translational movement between the locking sleeve 100 and the cuff 96. Therefore, the screwing engagement between the locking sleeve 100 and the latch 98 functionally results in translational movement of the latch 98 in the direction of arrow 102 (FIG. 6). While threads 110 are depicted as being an integral part of the locking sleeve 100, in alternative embodiments, the threads 110 may be manufactured as a separate component (not depicted) that is fitted or secured into a fixed engagement with the locking sleeve 110.

The pawl 108 is constructed of a flexible or deformable material, such that if the tab 88 engages the toe 92 of the gas port 28 prior to the locking sleeve 100 completing a rotation, the compliance of the pawl 108 will permit the pawl 108 to jump into another thread 110 of the locking sleeve 100. Fixed grooves 115 disposed on an exterior surface 116 of the latch 98 are also configured to engage the threads 110 of the locking sleeve 100. The mating engagement of the grooves 115 with the threads 110 provides for a secure lock between the latch 98 and the locking sleeve 100.

The locking sleeve 100 is moved from the locked configuration to the unlocked configuration by rotating the locking sleeve in the direction opposite arrow 106. This threadingly disengages the pawl 108 and the fixed grooves 115 from the threads 110 and realign the cutout 104 with the finger 90 which again permits the outward deflection of the finger 90 to remove the tab 88 from engagement with the annular cutout 30 and the gas port 28. If, in an embodiment, the pawl had jumped one or more threads 100 as described above, a ramp 118 located on the locking sleeve 100 further provides a separate force against the latch 98, such as to cause the pawl 108 to deform and jump back into its original alignment. It is to be recognized that in alternative embodiments, the ramp 118 engages a particular structure or ridge exemplarily depicted as ramp 124 on the latch 98. In an alternative embodiment, the ramp 124 of the latch engages any of a variety of structure on the locking sleeve 100 to achieve a similar result.

In a still further aspect of some embodiments of the locking sleeve 100, some embodiments of the locking sleeve 100 include a window 120, or alternatively, a plurality of windows 120 formed in the locking sleeve 100. The windows 120 selectively expose one or more visual indications 122 located on the cuff 96. The visual indications 112 are disposed about the cuff 96, such that dependent upon the orientation of the locking sleeve 100 about the cuff 96, a visual indication 122 is provided through the window 120, identifying the status of the connector 86, namely, whether the connector 86 is in a locked configuration or an unlocked configuration.

Figure 9:
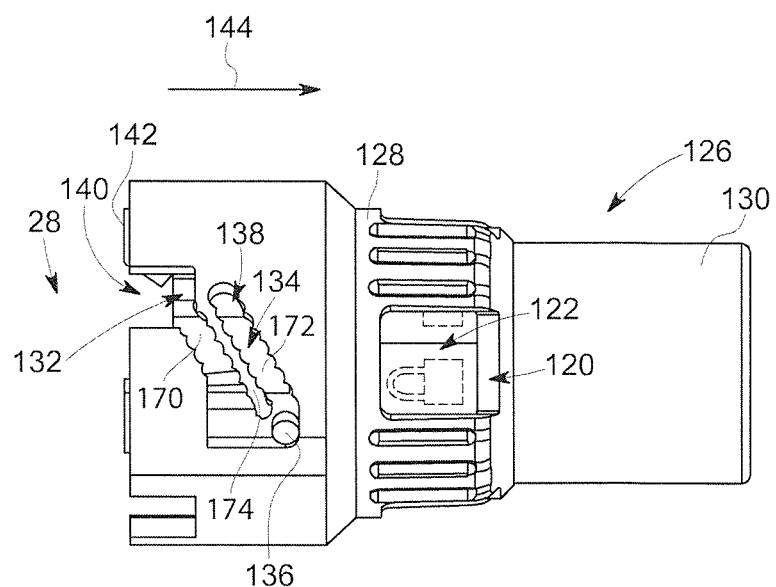
FIG. 9 depicts an alternative embodiment of a connector.

FIG. 9 depicts a still further embodiment of a connector 126. The connector 126 is similar to that disclosed above, particularly with respect to FIGS. 6-8. The connector 126 of FIG. 9 provides an additional depiction of the window 120 located in the locking sleeve 128 and the visual indication 122 of the cuff 130 visible through the window 120.

The connector 126 provides an additional embodiment for the interaction between the locking sleeve 128 and the latch 132. Rather than the threaded engagement as disclosed above with respect FIGS. 6-8, the locking sleeve 128 includes a cam 134 that is engaged by a cam follower 136 of the latch 132. The cam 134 includes a plurality of steps or ratchets 138 that each individually engage the cam follower 136 through a plurality of discrete steps to move the locking sleeve 128 from the unlocked configuration to the locked configuration or from the locked configuration to the unlocked configuration. It is understood that a variety of cam surfaces may be used in embodiments including smooth or saw-toothed cam surfaces. Similar to other embodiments, the locking sleeve 128 includes a cutout 140 that when aligned with a finger 142 of the latch 132, permits radially outward deflection of the finger 142. The cam follower 136 is positioned on the latch 132 in a position such that the rotation of the locking sleeve and engagement of the cam 134 with the cam follower 136, draws the latch 132 in the direction of arrow 144 as the locking sleeve 128 is rotated.

In the embodiment of the connector 126 depicted in FIG. 9, the cam 134 includes a first cam 170 and a second cam 172 separated by a resilient divider 174. In embodiments, the resilient divider 174 can act as a torque limiter by slightly deflecting upon engagement with the cam follower 136. This can help to eliminate slop in the connection by providing an additional force on the follower 136, particularly in embodiments wherein the cam 134 has discrete steps or engagements for the cam follower 136. Additionally, the resilient divider 174 can act in a similar function to the pawl and threads as described above with respect to FIGS. 6-8 in that if the finger completely engages a toe of the gas port, then the resilient divider 174 can deflect to some degree to accommodate the engagement. It is to be understood that in alternative embodiments, the cam 134 can be implemented with only a single cam in which case the resilient divider 174 would not be a feature.

In an alternative embodiment to be described in relation to FIG. 9, the cam follower 136 is not a portion of a latch, but rather is a separate component that is connected to a biasing device, exemplarily a spring located radially interior of the locking sleeve 128. In such an embodiment, the locking sleeve 128 may be configured to interact with the at least one finger in a manner as described above with respect to FIGS. 2-5. In operation, as the gas port is inserted into the connector 126, the gas port compresses the biasing device which moves the cam follower 136. The movement of the cam follower 136 along the cam surface 134 of the locking sleeve 128 causes the locking sleeve 128 to rotate, translate, or both, dependent upon the shape of the cam 134. In such an embodiment, thus the translational force applied between the gas port and the connector, causes the locking sleeve 128 to move between the unlocked and locked configurations.

Figure 10:
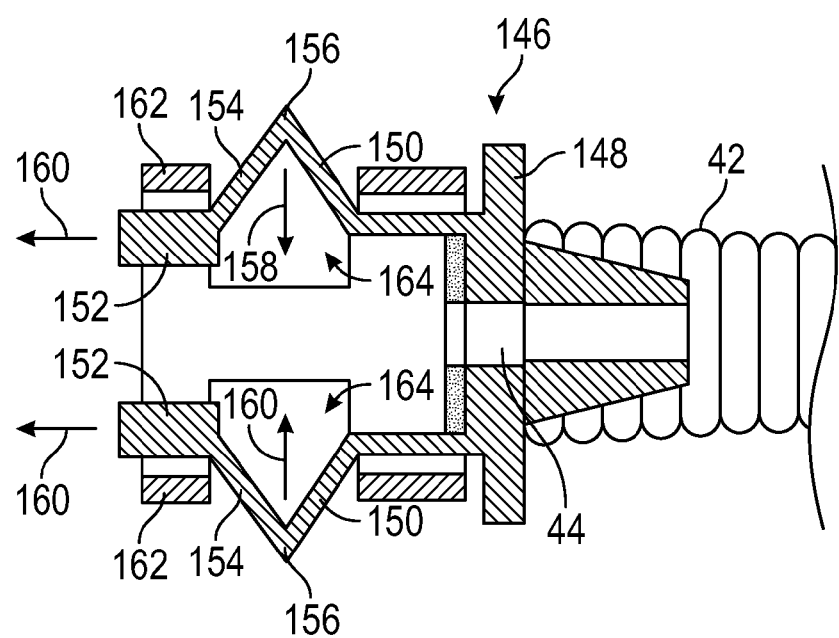
FIG. 10 is a cut away view of a still further embodiment of a connector in accordance with the embodiments disclosed herein.

FIG. 10 depicts a still further embodiment of a connector 146. The connector 146 is a two piece connector, and therefore incorporates elements of many of the embodiments as disclosed above, as well as some other features disclosed herein.

The connector 146 includes a cuff 148 from which extends a finger 150. The finger 150 terminates in a tab 152 that is configured to engage an annular cutout of a gas port (not depicted) as described in alternative embodiments above. It is to be recognized that in alternative embodiments a variety of number of fingers 150 may be present within the scope of the present disclosure. The finger 150 includes a projection 154 that projects radially outward from the cuff 148. The projection 154 radially terminates at a hinge 156. The hinge 156 may be its own structural component, or in an alternative embodiment, may be a living hinge formed in the finger 150. It will be appreciated that deflection of the finger 150 at the hinge 156 radially inward in the direction of arrow 158 will cause the projection 154 of the finger 150 to translate the tab 152 outward in the direction of arrow 160. Thus, radially inward deflection of the finger 150 in the direction of arrow 158 causes the finger 150 to extend beyond the locking sleeve 162. The extension of the finger 150 beyond the locking sleeve 162 allows the finger 150, and particularly the tab 152 to deflect radially outward such as to be moved past a toe of a gas port (not depicted) such as disclosed above. The return of the projection 154 back into the orientation depicted in FIG. 10, results in the retraction of the finger and the tabs 152 back within the locking sleeve 162, thereby removing any slack that may exist between the tab 152 and the toe of the gas port (not depicted). In an alternative embodiment, one or more additional tabs (not depicted) may project radially inward from the finger 150 or projection 154. The additional tabs may define alternative locations for the connector to engage a toe of the gas port as described above.

It will be recognized that the locking sleeve 162 includes an opening 164 such as for the projection 152 to outwardly project. Various embodiments of the locking sleeve 162 can facilitate various manners in which the projection 154 is deflected and returned. In one embodiment, the locking sleeve 162 translates outward in the direction of arrow 160, thereby using a translating force on the projection 154 and the finger 150 as a whole. In an alternative embodiment, the locking sleeve 162 rotates and the shape of the opening 164 progressively narrows to slide past the projection 154 forcing the projection radially inwards in the direction of arrow 158. However, these are intended to be merely exemplary embodiments on the mechanics of such an interaction between the locking sleeve 164 and the finger 150, and it will be recognized that alternative embodiments are considered to be within the scope of the present disclosure.

Figure 11:
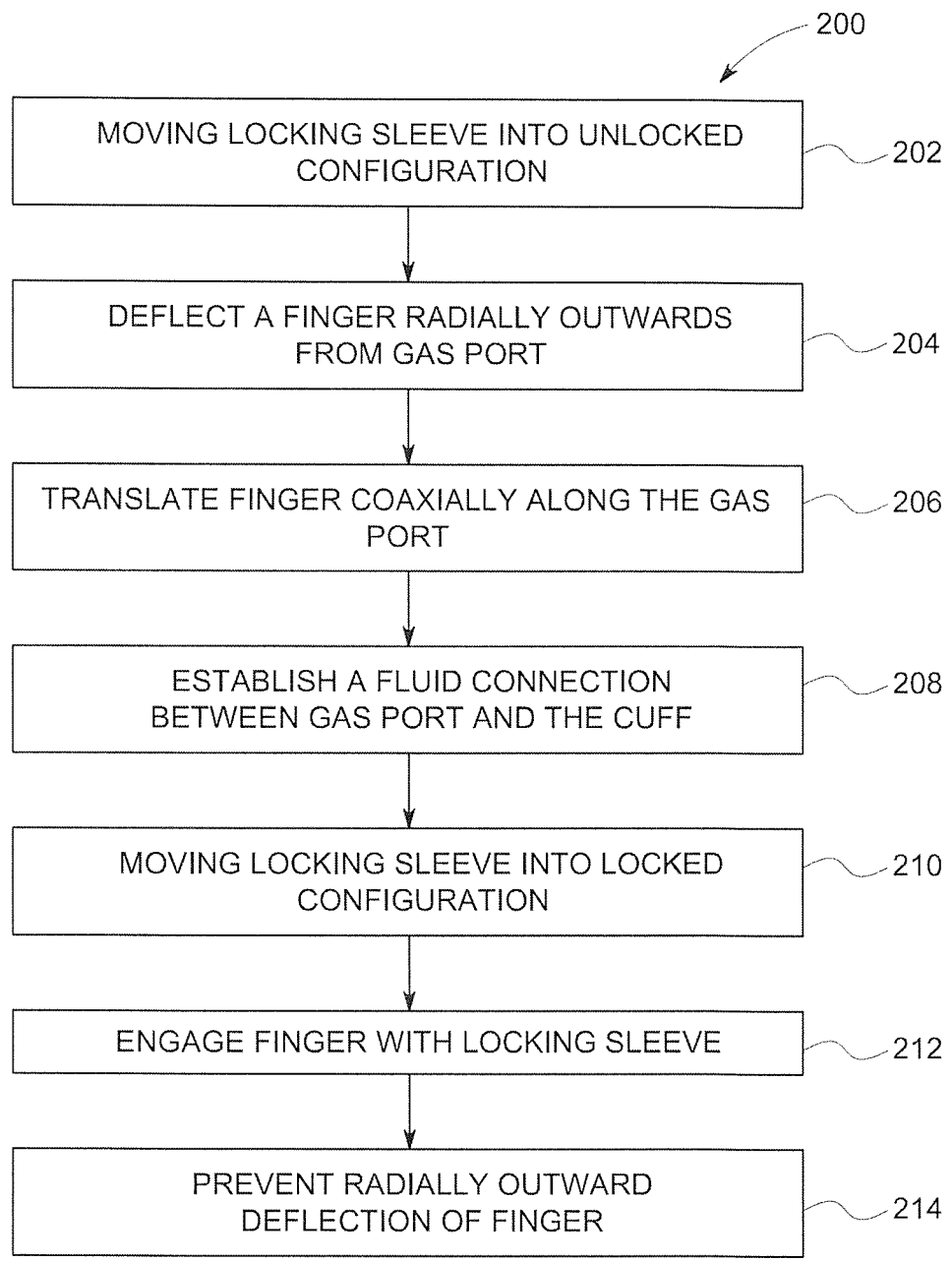
FIG. 11 is a flow chart that depicts an embodiment of a method in accordance with the embodiments disclosed herein.

FIG. 11 is a flow chart that depicts an embodiment of a method 200 of universal connection to a gas port. The method 200 begins by moving a locking sleeve into an unlocked configuration at 202. As disclosed above, a locking sleeve can be coaxially aligned with at least a portion of a cuff of a connector and the locking sleeve is movable between a locked configuration and an unlocked configuration. Non-limiting examples of the manners in which the locking sleeve can be moved into an unlocked configuration have been disclosed with respect to the embodiments above.

Next, at 204 a finger of a connector is deflected radially outwards from the gas port. As disclosed with respect to the embodiments disclosed above, the finger deflects radially outward such as to move past at least a front end portion of the gas port. At 206 the finger, after being deflected radially outward, is translated coaxially along the gas port. The finger is translated coaxially along the gas port at 206 until a fluid connection is established between the gas port and the cuff of the connector at 208. Therefore, the radially outward deflection and the translation of the finger enables the finger to move about and past the gas port in order to establish the fluid connection between the gas port and the cuff of the connector.

After the fluid connection is established at 208, the locking sleeve is moved into a locked configuration at 210. The non-limiting embodiments disclosed above provide numerous examples of manners in which the locking sleeve can achieve a locked configuration for 210. In the locked configuration, the finger is engaged with the locking sleeve at 212 and this engagement prevents the finger from deflecting radially outward at 214. Thus, the method 200 establishes a fluid connection between a gas port and a cuff and further prevents disconnection between the connector and the gas port by securing the finger from radially outward deflection as would be required to translate the fingers off of the gas port to remove the connector from the gas port. In addition to the method 200 as described above, still further embodiments specifically seek to provide a connection to a gas port that includes an annular cutout, as described with respect to non-limiting embodiments disclosed herein. In some embodiments of alternative methods for connecting to a gas port with an annular cutout, the locking sleeve further translates the finger in the direction of the connector, such as to remove any slack between the finger and the annular cutout. In still further embodiments, the finger includes a tab at an outer end of the finger, and the tab of the finger engages both the annular cutout and a toe at an end of the gas port.

It is understood that while the present disclosure provides a variety of examples of embodiments, these are intended to be merely exemplary and still further embodiments are considered to be within the scope of this disclosure that combine features of the disclosed embodiment, although not appearing in specific combination. Also, while the description as focused on the specific fluid of medical gas, it is understood that embodiments of the connector as disclosed herein can be used for any of a variety of fluids, including liquids or gases.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A fluid delivery connection, comprising: a cuff that is configured to engage a port and connect to a fluid delivery circuit, such as to create a fluid connection between the port and the fluid delivery circuit, an outermost surface of the cuff defining a first radius from a center of the cuff; a finger extending away from the cuff, the finger configured to interact with the port; and a locking sleeve movably disposed at least partially about the cuff and the finger, wherein the locking sleeve is selectively movable between an unlocked configuration wherein the finger is movable and a locked configuration wherein the finger is secured to the port, the locking sleeve consisting of a plurality of interconnected discontinuous ramps wherein each ramp comprises an inner surface having a continuously varying inner diameter throughout the ramp such that the inner surface is configured to progressively engage the finger as the locking sleeve is moved from the unlocked configuration to the locked configuration, the ramp extending radially and inwardly of the first radius.

2. The fluid delivery connection of claim 1, further comprising a latch movably secured to the cuff and to the locking sleeve, wherein the latch comprises the finger.

3. The fluid delivery connection of claim 2, wherein the latch and locking sleeve are complementarily keyed such that movement of the locking sleeve from the unlocked configuration to the locked configuration draws the latch towards the cuff, which secures the finger to the port.

4. The fluid delivery connection of claim 3, further comprising a cutout in the locking sleeve, wherein the finger of the latch selectively fits within the cutout when the locking sleeve is in the unlocked configuration, the cutout in the locking sleeve permitting movement of the finger radially away from a central axis of the latch and wherein the finger of the latch is out of alignment with the cutout when the locking sleeve is in the locked configuration, the absence of alignment of the cutout and the finger retains the finger in engagement with the port.

5. The fluid delivery connection of claim 1, wherein the finger is integral with the cuff and the locking sleeve is coaxially disposed about the cuff, the locking sleeve at least partially rotates about the cuff and the finger to secure the finger to the port.

6. The fluid delivery connection of claim 5, further comprising a wedge disposed along an interior surface of the locking sleeve, wherein rotation of the locking sleeve applies pressure to the finger to secure the finger to the port.

7. The fluid delivery connection of claim 1, wherein the finger is integral with the cuff and the locking sleeve is coaxially disposed about the cuff, the locking sleeve at least partially translates along the cuff and the finger to secure the finger to the port.

8. The fluid delivery connection of claim 1, wherein the fluid delivery connection is configured to provide medical gas, the port is a medical gas port, and the fluid delivery circuit is a breathing circuit configured to provide medical gas to a patient.

9. A gas delivery system comprising: a gas port with an annular cut out; a breathing circuit configured to be connected to a patient to deliver medical gas to the patient; a cuff with a first end that removably engages the breathing circuit and a second end that removably engages the gas port, wherein the cuff creates a fluid connection between the gas port and the breathing circuit; a finger that selectively engages the gas port, the finger comprising a tab that selectively engages the annular cut out of the gas port; and a locking sleeve disposed about at least a portion of the cuff, the locking sleeve being selectively movable between an unlocked configuration wherein the finger is movable and a locked configuration wherein the finger is secured to the gas port and the tab is secured to the annular cut out of the gas port, the locking sleeve comprising a ramp extending radially inward from an inner surface of the locking sleeve, a first end of the ramp extending to a first distance, a second end of the ramp extending to a second distance greater than the first distance, the ramp having an increasing radial width from the first end to the second end such that the ramp is configured to progressively engage the finger as the locking sleeve is moved from the unlocked configuration to the locked configuration, the locking sleeve comprising a cutout extending through an interior surface and an exterior surface along a perimeter of the locking sleeve, the cutout configured to permit the finger to move radially outward when the locking sleeve is in the unlocked configuration.

10. The gas delivery system of claim 9, further comprising: a latch coaxially disposed between the cuff and the locking sleeve, the latch comprising the finger.

* * * * *